United States Patent [19]
Pratt

[11] Patent Number: 4,832,964

[45] Date of Patent: May 23, 1989

[54] PREPARATION OF A BLUE CHEESE FLAVOUR

[75] Inventor: Nadine G. Pratt, Bantam, Conn.

[73] Assignee: Nestec S.A., Vevey, Switzerland

[21] Appl. No.: 112,254

[22] Filed: Oct. 22, 1987

[51] Int. Cl.$^4$ .............................................. A23L 1/221
[52] U.S. Cl. ...................... 426/33; 426/650; 426/601
[58] Field of Search ............. 426/7, 33, 34, 35, 37, 426/42, 43, 61, 62, 601–602, 606–608, 650

[56] References Cited

U.S. PATENT DOCUMENTS

| | | | |
|---|---|---|---|
| 2,794,743 | 6/1957 | Farnham | 99/56 |
| 3,072,488 | 1/1963 | Watts et al. | 426/37 |
| 3,100,153 | 8/1963 | Knight | 426/35 |

FOREIGN PATENT DOCUMENTS 1361817  7/1974  United Kingdom .

*Primary Examiner*—Marianne Cintins
*Attorney, Agent, or Firm*—Vogt & O'Donnell

[57] ABSTRACT

A blue cheese flavorant is prepared by first hydrolyzing a reaction medium of an animal or vegetable fats and oils having $C_4$ to $C_{14}$ triglycerides with an enzyme which liberates $C_4$ to $C_{14}$ fatty acids from the fats and oils in a reaction mixture. A culture medium containing the liberated fatty acids, and which may include unhydrolyzed fats and oils from the reaction mixture, is prepared and inoculated with spores of *Penicillium roqueforti*. The inoculated culture medium is fermented under submerged aerobic conditions while being agitated. The fermented culture medium then is pasteurized for deactivating the spores and a blue cheese flavorant product is obtained from the pasteurized, deactivated culture medium. Alternatively, $C_4$ and $C_{14}$ fatty acids alone may be fermented to obtain the flavorant.

23 Claims, No Drawings

PREPARATION OF A BLUE CHEESE FLAVOUR

BACKGROUND OF THE INVENTION

The present invention relates to the preparation of a flavouring substance and more particularly, to a process for the preparation of a flavouring substance having a blue cheese flavour.

Methods have been described for preparing flavours such as blue cheese flavours by means of submerged culture fermentation of media containing milk materials and fats or oils with cultures of *Penicillium roqueforti*, e.g., U.S. Pat. No. 3,100,153, U.S. Pat. No. 3,072,488 and British Pat. No. 1361817. In the processes described in these patents, the presence of milk products such as whole milk, skim milk, cream, curd or whey is required and the fermentation step takes at least two days.

SUMMARY OF THE INVENTION

We have found, surprisingly, that good yields of blue cheese flavouring substances can be obtained by means of submerged culture fermentation in the absence of milk products and wherein the fermentation step takes significantly less than 24 hours.

Accordingly, the present invention provides a process for the preparation of a flavouring substance which comprises fermenting free fatty acids or salts thereof with agitation in a culture medium inoculated with *Penicillium roqueforti* under submerged aerobic conditions and pasteurising the liquid product obtained. Advantageously, the free fatty acids or salts thereof are produced by hydrolysing a fat or oil of animal or vegetable origin.

During the fermentation, the free fatty acids or salts thereof are metabolised into methyl ketones which provide some of the predominant flavour volatiles of blue cheese.

DESCRIPTION OF THE PREFERRED EMBODIMENTS

The fatty acids or salts thereof utilized in the present invention are preferably of lower to mid chain length, for example, $C_4$ to $C_{14}$ and especially $C_6$ to $C_{12}$ fatty acids which may be liberated from fats and oils having $C_4$ to $C_{14}$ triglycerides.

The aeration is conveniently achieved by passing air through the culture medium, for instance at a rate of from 200 to 1500 cc/min, preferably from 400 to 1200 cc/min and especially from 600 to 1000 cc/min.

Although the quantity of the free fatty acids or salts thereof used in the culture medium may be up to, for instance, 10% by weight, the desired flavour may be obtained with much less, for example, from 0.5 to 5%, preferably from 0.75 to 4%, and especially from 1 to 3% by weight based on the total weight of the culture medium.

The free fatty acids or salts thereof may be incorporated in the culture medium in the form of the mixture obtained by the hydrolysis of the oil or fat, comprising fatty acids or salts thereof, unhydrolysed oil and water.

The culture medium also contains water, the total amount of which is conveniently from 50 to 95% and preferably from 70 to 80% by weight based on the total weight of the culture medium. The culture medium may also optionally contain sodium citrate in an amount of, for example, up to 4%, preferably from 0.5 to 1.0% by weight and dextrose in an amount of, for example, up to 6.0% and preferably from 0.5 to 1.0% by weight, based on the total weight of the culture medium.

The fermentation may be carried out in either a sterilisable fermenter or a sanitized closed jacketed vessel. If a sanitized closed jacketed vessel is used, the water should be first sterilised, for instance, by boiling.

The pH of the fermentation mixture may be, for instance, from 4.0 to 8.0, preferably from 5.0 to 7.0 and especially from 5.9 to 6.1.

Although *Penicillium roqueforti* mycelia may be used in the fermentation, the spores are preferred because the mycelial stage has a tendency to metabolise the methyl ketones further whereas the spore stage does not and because the mycelia are more susceptible to fatty acid toxicity than the spores. The spores are preferably used at a level of from $1 \times 10^6$ to $8 \times 10^8$ spores/gram and more usually from 4 to $6 \times 10^8$ spores per gram. They may conveniently be used at a concentration of from 1 to 6 gm/100 ml and preferably from 3 to 5 gm/100 ml in the fermentation. The spores may, if desired, be cultured and then centrifuged to a pellet which can be used as the inoculum, or they may be used on bread crumbs.

Although methyl ketones can be detected by gas chromatography after 3 hours, the fermentation may proceed for up to approximately 72 hours. However, it is preferred that the fermentation is allowed to proceed for a period of from 6 to 30 hours, while a duration from 8 to 24 hours usually provides the optimum flavour production.

By the fermentation process a liquid product is obtained which is pasteurised by any conventional method to deactivate the *Penicillium roqueforti*, for example, by means of a high temperature-short time treatment. The liquid product may then be separated into the oil and water fractions and the oil fraction which contains most of the methyl ketones can be used as the flavouring agent itself. Alternatively, the liquid product, after pasteurisation, may be made into a paste by concentrating the flavour by conventional means such as reverse osmosis or volatile stripping and used as a flavour either by itself or in admixture with dairy solids. In another variation, the liquid product, after pasteurisation may be spray dried using carriers such as maltodextrins or milk solids, etc., and used as a flavour.

The fat or oil from which the fatty acids are produced by hydrolysis may be of animal origin such as butterfat from milk or a vegetable derived fat, preferably coconut oil. Advantageously, the fat contains lower to mid-chain length fatty acids, especially $C_6$ to $C_{12}$ fatty acids which may be liberated from fats and oils having $C_6$ to $C_{12}$ triglycerides.

The fat or oil can be hydrolyzed by any conventional means such as chemically using NaOH, enzymatically using lipases or by high temperature and pressure to produce the free fatty acids. The preferred enzyme is one that liberates $C_4$–$C_{14}$ fatty acids from oils or fats. They may be derived from the following micro-organisms: Mucor sp., *Aspergillus niger*, *Rhizopus oryzae*, *Candida cylindracea*, Penicillum sp. or from animal origin such as pancreatic lipase from porcine pancreas. The preferred method of lipolysis is by using a lipase derived from *Rhizopus oryzae*.

The amount of oil or fat used in enzyme hydrolysis may be from 5 to 25% by weight and preferably from 15 to 20% by weight based on the total weight while the amount of water may be from 75 to 95% by weight and preferably from 80 to 85% by weight. The amount of enzyme is conveniently from 0.025 to 0.25% and preferably from 0.05 to 0.15% by weight based on the total weight of the hydrolysis reaction medium. The hydrolysis time, temperature and pH depend on the particular enzyme employed but, typically, the time ranges from 0.5 to 2.0 hours, the temperatures ranges from 25° C. to 45° C. and the pH ranges from 4 to 8. When using a lipase derived from *Rhizopus oryzae,* the preferred temperature is from 35° to 40° C., the preferred time is from 45 to 75 minutes and the pH is preferably maintained at a value from 6.5 to 7.5 using a buffer such as sodium hydroxide or a phosphate, etc. The use of sodium hydroxide is preferred to produce the sodium salts of the fatty acids.

After hydrolysis, the hydrolysed oil or fat is conveniently heat treated to deactivate the enzyme. Any conventional method of heat treatment may be employed, for example, a high temperature short time treatment. By this hydrolysis process a mixture comprising the hydrolysed fat or oil usually together with about 40-60% unhydrolysed oil in water is obtained, which may advantageously be used as the fatty acid source for the fermentation process in the culture medium, if desired, after separation from the unhydrolysed oil.

EXAMPLES

The following examples further illustrate the present invention. Parts and percentages are given by weight unless otherwise indicated.

Example 1

(A) Production of Hydrolyzed Coconut Oil

Seventeen parts of coconut oil were heated to 35°-40° C. Then 79 parts of water were added to the coconut oil. This mixture was heated to 37° C. A slurry of 4 parts of water and 0.1 parts of lipase (from *Rhizopus oryzae* were added to the oil/water mixture. This mixture was agitated in an open vessel using a polytron, from the Tekmar Company, at 37° C. for 1 hour. The pH was monitored and maintained at pH 7.0 with 5-10 parts of a 25% NaOH solution throughout the reaction. The temperature was increased to 100° C. and maintained at 100° C. for 7 to 15 minutes depending on the sample size to deactivate the lipase. The hydrolyzed oil/water mixture is then used in the process of blue cheese flavor production.

(B) Preparation of the inoculum

A mixture of 0.5 parts dextrose, 0.5 parts of sodium citrate and 20 parts of water was made and vacuum filtered through a sterile filter (0.45 μm). 4 parts of *Penicillium roqueforti* spores (dried on bread crumbs—Midwest Blue Mold—Dairyland Food Labs) were added to the sterile filtrate mixture which was shaken to disperse the spores into the water to make a slurry.

(C) Production of blue cheese flavor

Seventeen parts of hydrolyzed coconut oil/water from part A of this example containing 14 parts water, 1.5 parts free fatty acids or salts thereof, and 1.5 parts unhydrolysed oil were mixed with 57.60 parts of water and put into either a sterilisable fermenter or a sanitized closed jacketed vessel. (If put into sanitized closed jacketed vessel, the water should be sterilized, i.e., boiling). The mixture whose temperature was 30° C. was agitated while the *Penicillium roqueforti* spore slurry prepared in part B of this Example was slowly added to the vessel. The pH of the reaction mixture was taken and if it was not at pH 6.0±0.1, the pH was then adjusted to 6.0 using 50% NaOH, if the solution was acidic, or 33%, HCl if the solution was basic.

Aeration was then sparged into the vessel at a rate of 800 cc./min/l. substrate. (The vessel contained another opening so the pressure would not build up but a positive air flow was maintained. The reaction was run for 8 hours keeping the temperature of the product at 30° C. with aeration and agitation continued throughout the 8 hour period. When the 8 hour period was finished the product was centrifuged or decanted to take the bread crumbs out which the spores had been inoculated on and then dried. The liquid product was then pasteurized to HTST to deactivate the *Penicillium roqueforti* spores. The product was separated into the oil and wate fractions. The oil layer contains most of the flavoring compounds (methyl ketones) and can be used as a flavoring by itself.

Example 2

A similar procedure to that described in Example 1 was followed but in which the pasteurised product from part C was made into a paste by concentrating the flavor via conventional means such as reverse osmosis, volatile stripping, etc., and used as a flavor by itself or in a mixture with dairy solids.

Example 3

A similar procedure to that described in Example 1 was followed but in which the pasteurised product from part C was spray dried using carriers such as maltodextrins, milk solids, etc.

I claim:

1. A process for the preparation of a blue cheese flavorant comprising fermenting a substance in a culture medium, wherein the substance to be fermented consists essentially of $C_4$ to $C_{14}$ free fatty acids including salts thereof, with spores of *Pencillium roqueforti* under submerged aerobic conditions while agitating the culture medium for metabolizing the fatty acids to methyl ketones and pasteurizing the fermented culture medium for deactivating the spores thereby obtaining a liquid product having a blue cheese flavor.

2. A process according to claim 1 wherein the free fatty acids consist essentially of $C_6$ to $C_{12}$ free fatty acids.

3. A process for the preparation of a blue cheese flavorant comprising hydrolyzing a substance in an aqueous reaction medium, wherein the substance is selected from a group consisting of vegetable substance having $C_4$ to $C_{14}$ triglycerides, for liberating $C_4$ to $C_{14}$ fatty acids from the substance in a reaction mixture, preparing a culture medium with free fatty acids which consist essentially of the fatty acids liberated by the hydrolysis of the vegetable substance and with unhydrolyzed vegetable substance remaining from the hydrolysis of the vegetable substance lipids, inoculating the culture medium with spores of *Pencillium roqueforti,* fermenting the inoculated culture medium under submerged aerobic conditions while agitating it for metabolizing free fatty acids into methyl ketones and pasteurizing the fermented culture medium for deactivating the spores thereby obtaining a liquid product having a blue cheese flavor.

4. A process according to claim 3 wherein the substance is coconut oil.

5. A process for the preparation of a blue cheese flavorant comprising hydrolyzing a substance having $C_4$ and $C_{14}$ triglycerides in an aqueous reaction medium with an enzyme derived from an organism selected from a group consisting of Mucor sp., *Aspergillus niger*, *Rhizopus oryzae*, *Candida cylindracea* and Penicillium sp. for liberating $C_4$ to $C_{14}$ free fatty acids from the substance in a reaction mixture, heat-treating the reaction mixture for deactivating the enzyme, preparing a culture medium which includes the liberated free fatty acids of the enzyme deactivated reaction mixture, inoculating the culture medium with spores of *Pencillium roquerforti*, fermenting the inoculated culture medium under submerged aerobic conditions while agitating it for metabolizing the free fatty acids into methyl ketones and pasteurizing the fermented culture medium for deactivating the spores thereby obtaining a liquid product having a blue cheese flavor.

6. A process according to claim 5 wherein the substance is selected from a group consisting of vegetable fats and oils.

7. A process according to claim 5 wherein the culture medium is prepared with the enzyme deactivated reaction mixture which includes the fatty acids and unhydrolyzed substance.

8. A process according to claim 5 wherein the substance is coconut oil.

9. A process according to claim 8 wherein the only free fatty acids of the culture medium are the free fatty acids liberated from the hydrolysis of the coconut oil.

10. A process according to claim 8 wherein the culture medium is prepared with the reaction mixture which includes free fatty acids liberated from the coconut oil and unhydrolyzed coconut oil and the only fatty acids and oil of the culture medium are those from the reaction mixture.

11. A process according to claim 5 wherein the substance consists essentially of coconut oil.

12. A process according to claim 11 wherein the only free fatty acids of the culture medium are free fatty acids liberated from the hydrolysis of the coconut oil.

13. A process according to claim 11 wherein the culture medium is prepared with the reaction mixture which includes free fatty acids liberated from the coconut oil and unhydrolyzed coconut oil and the only fatty acids and oil of the culture medium are those of the reaction mixture.

14. A process according to claim 5 wherein the substance to be hydrolyzed is in an amount of from 5% to 25% by weight based upon the total weight of the reaction medium, the enzyme is in an amount of from 0.025% to 0.25% by weight based upon the total weight of the reaction medium and the hydrolysis is carried out at a temperature of from 25° C. to 45° C. for from 0.5 hours to 2.0 hours at a pH of from 4 to 8.

15. A process according to claim 14 wherein the substance to be hydrolyzed is in an amount of from 15% to 20% by weight based upon the total weight of the reaction medium, the enzyme is in an amount of from 0.05% to 0.15% by weight based upon the total weight of the reaction medium and the hydrolysis is carried out at a temperature of from 35° C. to 40° C. for from 45 minutes to 75 minutes at a pH of from 6.5 to 7.5.

16. A process according to claim 5 wherein the culture medium contains water in an amount of from 50% to 95% by weight based on the total weight of the culture medium and contains free fatty acids in an amount of from 0.5% to 5% by weight based on the total weight of the culture medium and wherein the spores for inoculating the culture medium are at a level of from $1 \times 10^6$ to $8 \times 10^8$ spores per gram and are inoculated into the culture medium in an amount of from 1 gm/100 ml to 6 gm/100 ml.

17. A process according to claim 16 wherein the culture medium contains water in an amount of from 70% to 80% by weight based upon the total weight of the culture medium and contains free fatty acids in an amount of from 0.75% to 4% by weight based on the total weight of the culture medium and wherein the spores for inoculating the culture medium are at a level of $4 \times 10^8$ spores/gram to $6 \times 10^8$ spores/gram and are inoculated into the culture medium in an amount of from 3 gm/100 ml to 5 gm/100 ml.

18. A process according to claim 5 wherein the culture medium further comprises sodium citrate in an amount of up to 4% by weight based on the total weight of the culture medium.

19. A process according to claim 5 wherein the culture medium further comprises dextrose in an amount of up to 6% by weight based upon the total weight of the culture medium.

20. A process according to claim 5 wherein air is passed through the fermenting culture medium at a rate of from 200 cc/min to 1500 cc/min for obtaining the submerged aerobic conditions.

21. A process according to claim 5 further comprising separating water and oil fractions of the liquid product for obtaining the oil fraction for obtaining a blue cheese flavorant.

22. A process according to claim 5 further comprising concentrating the liquid product for forming a paste for obtaining a blue cheese flavorant.

23. A process according to claim 5 further comprising spray drying the liquid product for obtaining a blue cheese flavorant.

* * * * *

UNITED STATES PATENT AND TRADEMARK OFFICE
CERTIFICATE OF CORRECTION

PATENT NO. : 4,832,964

DATED : May 23, 1989

INVENTOR(S) : Nadine G. Pratt

It is certified that error appears in the above-identified patent and that said Letters Patent is hereby corrected as shown below:

Column 4, line 56 [line 11 of claim 3], delete "lipids".

Column 5, line 2 [line 5 of claim 5], "Mucor" should be italicized.

Signed and Sealed this

Third Day of April, 1990

*Attest:*

HARRY F. MANBECK, JR.

*Attesting Officer*      *Commissioner of Patents and Trademarks*